5,503,836

United States Patent [19]
Fellers et al.

[11] Patent Number: 5,503,836
[45] Date of Patent: Apr. 2, 1996

[54] METHODS FOR CONTROL AND MITIGATION OF MOLLUSCS

[75] Inventors: Billy D. Fellers, Glen Rose, Tex.; Thomas M. Laronge, Vancouver, Wash.; Arthur J. Freedman, Lebanon, N.J.

[73] Assignee: Electric Power Research Institute, Palo Alto, Calif.

[21] Appl. No.: 568,492

[22] Filed: Aug. 16, 1990

[51] Int. Cl.⁶ .................................................. A01N 25/32
[52] U.S. Cl. ........................................... 424/405; 424/406
[58] Field of Search ..................................... 424/405, 406, 424/78; 514/493

[56] References Cited

U.S. PATENT DOCUMENTS

| | | | |
|---|---|---|---|
| 3,285,809 | 11/1966 | Mod et al. | 514/625 |
| 4,073,939 | 2/1978 | Thompson et al. | 514/625 |
| 4,288,455 | 9/1981 | Haines | 514/477 |
| 4,643,835 | 2/1987 | Koeplin-Gall et al. | 210/754 |

FOREIGN PATENT DOCUMENTS

| | | |
|---|---|---|
| 351591 | 1/1990 | European Pat. Off. . |
| 1460037 | 10/1965 | France . |
| 60112701 | 6/1985 | Japan . |
| 804186 | 11/1958 | United Kingdom . |

OTHER PUBLICATIONS

I. Kubo I. Ymatsumato Y. A. Klacket Kamikawa Division of Entomology and Parasitology & Dept. of Chemistry (Japan) 18 May 1983.

C. A. 101:3936z I. Kubo et al 1984.
C. A. 103:191482m Nippon .. Ltd. 1985.
Database WIP Abstract, *"Mollusicidal N-(3-Chloro-4-Methylphenyl) Amides of Carboxylic Acids"*, Section Ch, Week H00, Dec., 1968.
Chemical Patents Index Abstract, Documentation Abstract Journal, *"Nippon Oils & Fats KK"*, Section Ch, Week 8531, Sep. 25, 1985.
Chemical Patents Index Abstract, Documentation Abstract Journal, *"Nippon Oils & Fats KK"*, Section Ch, Week 8530, Sep. 18, 1985.
Final Supplemental European Search Report EP 919150763.

*Primary Examiner*—Thurman K. Page
*Assistant Examiner*—P. Kulkosky
*Attorney, Agent, or Firm*—Fish & Richardson

[57] ABSTRACT

A method is provide for controlling the proliferation of molluscs in target habitat by applying to the habitat a compound or mixture of compounds which are fatty acid amides, disubstituted fatty amides, fatty acid alkanolamides and ethoxylated or propoxylated derivatives of amides, alkyl and aryl polyethoxylated or polypropoxylated primary and secondary alcohols, block copolymers of ethylene oxide and propylene oxide, fatty acid substituted alkyl-aminocarboxylic acids, substituted amido and aminosulfates and aminosulfonates, alkylphenoxy polyethoxy ethanols, and ethoxylated tallow diamines. The above compounds are generally classified as surfactants, penetrants, wetting agents, detergents or emulsifiers having either nonionic or amphoteric properties. The performance of these compounds and their mixtures are further defined by their hydrophilic to lipophilic ratio or HLB and by their solubility as defined by their cloud point temperature.

11 Claims, No Drawings

METHODS FOR CONTROL AND MITIGATION OF MOLLUSCS

BACKGROUND OF THE INVENTION

The present invention is directed to methods of control and mitigation of molluscs and in particular, the control of molluscs for macrofouling control within industrial cooling water systems and within municipal water supply systems. The bi-valve molluscs *Dreissena polymorpha* (Zebra mussel) and *Corbicula fluminea* (Asian clam) are macrofouling species capable of settling in the service water systems (SWS) of electric power stations, water treatment stations, and other industrial systems which use fresh water from lakes and streams for heat exchange purposes. These molluscs can grow in sizes to reduce or block flow in small diameter piping or heat exchangers. For *C. fluminea*, the problem primarily stems from the small juvenile molluscs which become suspended in intake waters and settle in low flow areas (such as the bottom of large diameter piping, pipe bends, reservoirs, etc.). Once settled in these flow areas, the juveniles grow rapidly to sizes that will block the small diameter tubings. After growing to sizes capable of fouling the system components, the *C. fluminea* may crawl or be carried by water currents from the low flow areas into high flow piping where they are transported to other areas where their shells become lodged as constrictions in the tubing, thereby restricting or blocking flow.

The mode of action of *D. polymorpha* is somewhat different. The small larvae are carried into the intake on water currents and settle in the low flow areas very similar to those described for *C. fluminea*. However, unlike *C. fluminea* which burrow into the sediment accumulated in the low flow areas, *D. polymorpha* adults produce proteinaceous byssal threads from abyssal gland at the base of their foot to attach to hard surfaces. Since the juvenile *D. polymorpha* preferentially settle on open, hard surfaces, but also attach on the shells of attached adults, mats of mussels many shells thick develop in low flow areas. Moreover, dead mussel shells and mats of mussel shells may break loose from the walls of the low flow areas and are carried into macrofouling sensitive components such as heat exchangers. Since the adults attach by byssal threads to hard surfaces (including boat hulls) and the larvae remain for extended periods in the plankton, *D. polymorpha* have extensive capacity for dispersal by both natural and human mediated mechanisms and it, along with *C. fluminea*, will become a major macrofouler of power station water systems and other raw water systems.

The conventional control for both *C. fluminea* and *D. polymorpha* in water systems primarily involves constant application of chlorine in free residual level of about 0.3 to 0.5 ppm. Even at these levels, continuous chlorination may not exclude *C. fluminea* and the presence of chlorine enhances corrosion rates. Additionally, chlorination is under close regulatory scrutiny in many areas. More recently, a number of nonoxidizing toxicants, typically known as biocides, have been used as molluscicides.

Unfortunately, these compounds are usually toxic to non-target aquatic species at or below their effective concentrations for mollusc control. Also, these compounds may not be well suited for application to potable water supplies. Therefore, there is a need to develop effective, environmentally acceptable, non-oxidizing molluscicides for control of bi-valve macrofouling.

Moreover, it would be desirable to provide such molluscicides which can be used at concentrations which can, on the one hand, control the proliferation of the molluscs, but on the other hand, be effective for that use at concentrations which are substantially lower than $LC_{50}$ levels for non-target species to improve their environmental acceptability and to further be suitable for potable applications. Many conventional oxidizing and non-oxidizing biocides which are utilized are so active by environmental protection standards, that they often require detoxification treatment to support their use. A molluscicide which does not require detoxification treatment would therefore be desired.

It is therefore an object of the present invention to provide a method for controlling proliferation of molluscs by applying a class of chemicals to this habitat which have been found to be effective to control their proliferation, particularly of *D. polymorpha* and *C. fluminea*, at effective concentrations which have a greater margin to $LC_{50}$ concentrations for non-target species and which are more acceptable for potable water systems.

It is a further object of the present invention to provide a method for controlling proliferation of molluscs utilizing chemicals which, in addition to their molluscicide activity, have a chemical effect on byssal attachment of molluscs as an additional macrofouling control mechanism.

These and other objects will be apparent from the following description and from the practice of the invention.

SUMMARY OF THE INVENTION

The present invention provides a method for controlling and mitigating macrofouling by molluscs, particularly *D. polymorpha* and *C. fluminea* which are present in the waters in the system in which macrofouling inhibition is required, treating these waters with a composition comprising one, or a mixture of compounds, selected from the group consisting essentially of amides, non-ionic alcohols, and ethers, and amphoteric amino acids. Preferred embodiments of use of such compounds are disclosed. The dosage of the composition required to effectively control the proliferation of the molluscs may be as low as about 1.0 mg/liter and up to as much as about 20 mg/liter depending on the selected treatment regime. Effective treatment regimes include, but are not limited to continuous low level applications, discontinuous or intermittent applications of low to medium concentrations, and higher level slug type treatments. These variations may be practiced under static or flowing conditions. The present invention provides control through mortality of the molluscs, by control of their attachment to, and by their detachment from substrates.

DESCRIPTION OF THE PREFERRED EMBODIMENTS

Particularly preferred amides include fatty acid amides, N,N-disubstituted fatty amides, fatty acid alkanolamides and ethoxylated or propoxylated derivatives of these amides. By fatty acids, it is meant those acids having a carbon chain backbone of from about 6 to 30 carbon atoms. Preferred non-ionic alcohols include polyethoxylated, polypropoxylated and/or aryloxylated primary and secondary alkyl and aryl alcohols. The alkyl or aryl alcohols will preferably have from 2 to about 20 carbon atoms. The preferred aryloxy group is an alkyl-phenoxy group. The preferred alkyl phenoxyl groups are octylphenoxy and nonylphenoxy.

Preferred ethers include block copolymers of ethylene oxide and propylene oxide, preferably of molecular weights in the range of about 100 to about 100,000. Finally, the preferred amphoteric amino acids include fatty acid substituted alkyl aminocarboxylic acids, amido and aminosulfates, and aminosulfonates.

Exemplary N,N-disubstituted amides of fatty acids include tall oil fatty acids. A particularly preferred class of N,N-disubstituted amides of fatty acids include the chemicals sold under the trademark BULAB by Buckman Laboratories. A particularly preferred amide is Bulab 8007 which is an N,N-disubstituted amide of tall oil fatty acids.

Exemplary ethoxylated or propoxylated alcohols include octylphenoxy-polyethoxy ethanols, nonylphenoxy-polyethoxy ethanol, and secondary alcohol ethoxylates. A particularly preferred class includes chemicals sold under the trademark of TERGITOL 15-S Series and TERGITOL Specialty Nonionic Surfactants by Union Carbide, and under the trademark of TRITON Series of non-ionic surface active agents by Rohm and Haas. Examples of these compounds include TERGITOL 15-S-3 (Union Carbide), a secondary alcohol ethoxylate; TRITON X-114 (Rohm and Haas Company), an octylphenoxy-polyethoxy ethanol; and TRITON N-101 (Rohm and Haas Company), a nonylphenoxy polyethoxy ethanol.

Exemplary ethers include polyalkylene glycol ethers. A particularly preferred class of polyalkylene glycol ethers includes the chemicals sold under the trademark of TERGITOL Specialty Nonionic Surfactants by Union Carbide. A particularly preferred ether is TERGITOL D-683 which is an oxirane methyl polymer with oxirane, mono (nonylphenyl) ether, branched.

Exemplary amphoterics include fatty acid substituted alkyl aminocarboxylic acids, substituted amido and amidosulfates and aminosulfonates. A particularly preferred class of substituted amino acid derivatives includes the chemicals sold under the trademark of DERIPHAT Amphoteric Surfactants by Henkel and under the trademark of ARMEEN Amphoterics by Akzo Chemicals. Two particular preferred amino acid derivatives include DERIPHAT 154-L, a disodium N-tallow beta-iminodipropionate by Henkel and ARMEEN Z, an N-coco alkyl-3-aminobutanoic acid (N-coco-beta-aminobutyric acid) by AKZO.

The present invention provides a method for controlling the proliferation of molluscs in a target habitat comprising the step of periodically or continuously applying to this habitat a composition comprising one, or a mixture of two or more, of the above-identified compounds. The nonionic compounds according to the present invention, are characterized by a cloud point range of up to 75° C. and a hydrophilic-lipophilic balance (HLB) range of about +5 to 15. The dosage, in general, of the composition required to effectively control the molluscs may be as low as about 1.0 mg/liter and up to as much as about 20 mg/liter based on the weight of the water containing the molluscs. The composition used in the present invention is particularly suited for a water system already set up with a halogen purification system (such as a chlorination purification system) and thus which is already equipped with appropriate apparatus for metering and introducing molluscicides into the water system, but is, of course, not limited thereto.

It will be apparent to those skilled in the art that, based on the discoveries explained herein, formulated products can be used to enhance performance in specific applications, both using molluscicides alone and with oxidizing biocides or other toxicants. It is apparent therefore that the above-identified compounds may be administered alone or in combination with other known molluscicides.

Static Testing

To illustrate the efficacy of the compounds utilized in accordance with the present invention, specimens of Zebra mussels (*D. polymorpha*) were obtained from various stations in the midwest United States and held in a 75 gallon tank, constantly aerated, refrigerated at about 50° F. until utilized in the tests. Also, Asian Clams (*C. fluminae*) were obtained from various water sources in the north central Texas area and were exposed to the same chemicals. The static tests were carried out at 68°–73° F. in a constant temperature laboratory in which the mussels were habituated for 7 days prior to any experimentation. The mussels were exposed to various concentrations of various agents within the scope of the present invention in 5 gallon plastic aquaria containing 4.5 gallons of an appropriate medium. Water in the test aquaria was constantly aerated and circulated. Media in the tanks were made by mixing appropriate concentrated stock solutions of the agents with dechlorinated tap water. Control tanks contained only the dechlorinated city water. Individual mussels of sizes ranging from recently settled juveniles, less than 1 centimeter long, to adults several years old, greater than 2.5 centimeters long, were tested. Samples of mussels (n=15 individuals per dish, 30 individuals in 2 dishes per tank, 210 mussels per experiment) were placed in 4×4×1 inch high glass dishes in the bottom of each 5 gallon test aquaria, initially containing only the dechlorinated city water. The shells of all mussels were etched with a permanent identifying mark and their shell length measured to the nearest 0.1 mm. Individuals were held in one of these dishes for 3 days prior to experimentation in the tanks to allow them to form byssal thread attachments. Another group of 15 individuals were placed in a second dish in each tank immediately prior to biocide exposure. This second group of mussels did not have time to form new byssal attachment threads before being exposed to the test agent. Thus, a group of 15 attached and 15 unattached mussels were placed in each of the 7 tanks (6 experimental, 1 control). Additionally 15 adult Asian clams were placed within each tank. Immediately after placement in the tanks, the appropriate amount of the chemical agent was added to achieve the desired test concentrations. Thereafter, the media in the tanks were replaced every 3 to 4 days to maintain chemical titre and to remove any waste products which could be deleterious the mussels. The behavior of the individuals, i.e., the number with open valves, normally syphoning water over the gills and the number with the valves shut were determined during each evaluation. The number of mussels attached and detached from the byssus were determined for each group in the tank, by probing each individual gently with a blunt glass rod. Byssally attached individuals cannot be displaced by gentle probing with a glass rod while unattached individuals are readily displaced. The number of living and dead individuals were determined at each observation. Dead mussels and clams were identified by gently touching the syphons and exposed mantle tissues at the posterior end of each individual in each sample with a blunt tip of a glass rod. The response to such stimulation to a living individual is to immediately clamp the valve shut. If no response is elicited, a second, stronger stimulation with the glass rod is given. If no valve closure response is observed after the second stimulation, an individual was considered dead. Upon death, individuals were removed from the test aquaria.

Further testing was conducted using the same protocol but limiting the exposure to chemicals for 24 hours, followed by placement in clean untreated waters. These tests were designed to study latent mortality in support of discontinuous treatment regimes.

The tests were conducted with successful results using those chemicals (A through N) listed in Table 1 which further discloses their physical properties.

TABLE 1

| Chemical Identification | | Critical Properties | |
|---|---|---|---|
| | Manufacturer | Cloud Point | HLB |
| Alcohols | | | |
| A. Tergitol 15-S-3 | Union Carbide | <0° C. | 8.0 |
| B. Tergitol TMN-3 | Union Carbide | <0° C. | 8.3 |
| C. Tergitol 15-S-5 | Union Carbide | <0° C. | 10.6 |
| D. Triton X-114 | Rohm & Haas | 22° C. | 12.4 |
| E. Tergitol Minifoam 2X | Union Carbide | 20° C. | |
| F. Tergitol 15-S-7 | Union Carbide | 37° C. | 12.1 |
| G. Tergitol Minifoam 1X | Union Carbide | 40° C. | |
| H. Triton N-101 | Rohm & Haas | 54° C. | 13.4 |
| I. Tergitol 15-S-9 | Union Carbide | 60° C. | 13.3 |
| J. Triton X-100 | Rohm & Haas | 65° C. | 13.5 |
| Amides | | | |
| K. Bulab 8007 | Buckman Labs | | |
| Ethers | | | |
| L. Tergitol D683 | Union Carbide | 21° C. | |
| Amphoterics | | | |
| M. Armeen Z | Akzo Chemical | | |
| N. Deriphat 154L | Henkel | | |

Efficacy Against Attached Adult *D. polymorpha*

The nonionic alcohols demonstrated excellent efficacy against attached *D. polymorpha* as shown in Table 2. These chemicals could be ranked by their performance in the order E>H>G>D>I>A>J>C>F>B.

The disubstituted amide of fatty acid, Chemical K, provided excellent efficacy against attached *D. polymorpha* and would be ranked better than Chemical E of the nonionic alcohols.

The performance of the ether compound, Chemical L, was above average when compared to the nonionic alcohols and would be ranked between Chemicals I and A.

The performance of the amphoterics against attached *D. polymorpha* is average for Chemical N. When compared to the anionic alcohols, Chemical N falls between Chemicals J and C and Chemical M falls between Chemicals F and B.

The overall ranking of the tested chemicals of this invention against attached *D. polymorpha* is in the order K>E>H>G>D>I>L>A>J>N>C>F>M>B.

TABLE 2

| Efficacy Against Attached *D. polymorpha* | | | | | | | | |
|---|---|---|---|---|---|---|---|---|
| | Days of Observation | | | | | | | |
| Chemical | 1 | 2 | 3 | 4 | 5 | 6 | 7 | 8 |
| 2A. Cumulative Mortality for Continuous Chemical Exposure | | | | | | | | |
| Controls | 0 | 0 | 0 | 0 | 0 | 0 | 0 | 0 |
| $A_{10}$ | 0 | 0 | 7 | 27 | — | 87 | | |
| $B_{10}$ | 0 | 0 | 0 | 0 | 0 | 7 | | |
| $C_{10}$ | 0 | 0 | 0 | 27 | 53 | | | |
| $D_{25}$ | 0 | 0 | 0 | 0 | 0 | 0 | 0 | 0 |
| $D_1$ | 0 | 0 | 0 | 0 | 0 | 0 | 0 | 0 |
| $D_5$ | 0 | 0 | 0 | 0 | 0 | 0 | 0 | 0 |
| $D_{10}$ | 0 | 15 | 23 | 31 | 92 | 100 | 100 | 100 |
| $E_{10}$ | 0 | 20 | 100 | 100 | 100 | 100 | | |
| $F_5$ | 0 | 0 | 0 | 0 | 13 | 13 | | |
| $F_{10}$ | 0 | 0 | 0 | 13 | 20 | | | |
| $G_5$ | 0 | 0 | 0 | 13 | 27 | 27 | | |
| $G_{10}$ | 0 | 0 | 25 | 75 | 100 | | | |
| $H_5$ | 0 | 0 | 33 | 87 | 100 | 100 | | |
| $H_{10}$ | 0 | 0 | 0 | 47 | 100 | 100 | | |
| $I_{10}$ | 0 | 0 | 13 | 67 | 100 | | | |
| $J_5$ | 0 | 0 | 0 | 0 | 0 | 0 | | |
| $J_{10}$ | 0 | 0 | 0 | 27 | 67 | | | |
| $K_{.25}$ | 0 | 0 | 0 | 0 | 0 | 0 | 0 | 0 |
| $K_1$ | 0 | 0 | 0 | 0 | 0 | 0 | 0 | 0 |
| $K_5$ | 13 | 80 | 93 | 93 | 93 | 93 | 93 | 93 |
| $K_{10}$ | 67 | 100 | 100 | 100 | 100 | 100 | 100 | 100 |
| $L_{10}$ | 0 | 0 | 0 | 56 | 63 | | | |
| $M_5$ | 0 | 0 | 0 | 0 | 0 | | | |
| $M_{10}$ | 0 | 0 | 0 | 0 | 13 | | | |
| $N_5$ | 0 | 0 | 0 | 0 | 0 | | | |
| $N_{10}$ | 0 | 0 | 0 | 43 | 43 | | | |
| 2B. Latent Mortality After 24 Hours Chemical Exposure | | | | | | | | |
| $D_{10}$ | 0 | 0 | 0 | 13 | 20 | 20 | | |
| $C_{10}$ | 0 | 0 | 47 | 60 | 73 | 73 | | |
| $H_{10}$ | 0 | 7 | 27 | 40 | 47 | 47 | | |
| $J_{10}$ | 0 | 0 | 13 | 13 | 13 | 13 | | |
| $K_{10}$ | 0 | 0 | 7 | 27 | 33 | 33 | | |

The subscript denotes concentration in mg/liter.

Efficacy Against Unattached Adult *D. polymorpha*

The nonionic alcohols demonstrated excellent and typically higher efficacy against unattached *D. polymorpha* as shown in Table 3. These chemicals could be ranked by their performance in the order D>E>H>G>C>F>J>A>B>I.

The disubstituted amide of fatty acid, Chemical K, provided excellent efficacy against unattached *D. polymorpha* and would be ranked better than Chemical D of the nonionic alcohols.

The performance of the ether compound, Chemical L, was average when compared to the nonionic alcohols and would be ranked between Chemicals F and J.

The performance of the amphoteric compounds against unattached *D. polymorpha* is fair. When compared to the nonionic alcohols, Chemical M falls between Chemicals B and I and Chemical N falls between Chemicals A and B.

The overall ranking of chemicals from this invention against unattached *D. polymorpha* is in the order K>D>E>H>G>C>F>L>J>A>N>B>M>I.

TABLE 3

| Efficacy Against Unattached *D. polymorpha* | | | | | | | | |
|---|---|---|---|---|---|---|---|---|
| | Days of Observation | | | | | | | |
| Chemical | 1 | 2 | 3 | 4 | 5 | 6 | 7 | 8 |
| 3A. Cumulative Mortality for Continuous Chemical Exposure | | | | | | | | |
| Controls | 0 | 0 | 0 | 0 | 0 | 0 | 0 | 0 |
| $A_{10}$ | 0 | 7 | 20 | 60 | — | 87 | | |
| $B_{10}$ | 0 | 0 | 0 | 7 | 13 | 13 | | |
| $C_{10}$ | 0 | 7 | 60 | 87 | 100 | | | |
| $D_{25}$ | 0 | 0 | 0 | 0 | 0 | 0 | 0 | 0 |
| $D_1$ | 0 | 0 | 0 | 0 | 7 | 20 | 20 | 20 |
| $D_5$ | 0 | 0 | 0 | 0 | 0 | 0 | 7 | 13 |
| $D_{10}$ | 0 | 73 | 100 | 100 | 100 | 100 | 100 | 100 |
| $E_{10}$ | 0 | 60 | 100 | 100 | 100 | 100 | 100 | 100 |
| $F_5$ | 0 | 0 | 0 | 0 | 7 | 7 | | |

TABLE 3-continued

Efficacy Against Unattached D. polymorpha

| Chemical | \multicolumn{8}{c}{Days of Observation} |
|---|---|---|---|---|---|---|---|---|
|  | 1 | 2 | 3 | 4 | 5 | 6 | 7 | 8 |
| $F_{10}$ | 0 | 0 | 13 | 93 | 100 |  |  |  |
| $G_5$ | 0 | 0 | 0 | 13 | 20 | 20 |  |  |
| $G_{10}$ | 0 | 0 | 80 | 93 | 100 |  |  |  |
| $H_5$ | 0 | 7 | 47 | 80 | 100 | 100 |  |  |
| $H_{10}$ | 0 | 0 | 80 | 100 | 100 |  |  |  |
| $I_{10}$ | 0 | 0 | 0 | 0 | 7 |  |  |  |
| $J_5$ | 0 | 0 | 0 | 0 | 0 | 0 |  |  |
| $J_{10}$ | 0 | 0 | 7 | 73 | 87 |  |  |  |
| $K_{.25}$ | 0 | 0 | 0 | 0 | 0 | 0 | 0 | 7 |
| $K_1$ | 0 | 0 | 0 | 0 | 0 | 0 | 0 | 0 |
| $K_5$ | 27 | 100 | 100 | 100 | 100 | 100 | 100 | 100 |
| $K_{10}$ | 67 | 100 | 100 | 100 | 100 | 100 | 100 | 100 |
| $L_{10}$ | 0 | 0 | 33 | 87 | 87 |  |  |  |
| $M_5$ | 0 | 0 | 0 | 0 | 0 |  |  |  |
| $M_{10}$ | 0 | 0 | 0 | 0 | 13 |  |  |  |
| $N_5$ | 0 | 0 | 0 | 7 | 7 |  |  |  |
| $N_{10}$ | 0 | 0 | 0 | 13 | 13 |  |  |  |
| \multicolumn{9}{l}{3B. Latent Mortality After 24 Hours Chemical Exposure} |
| $D_{10}$ | 0 | 0 | 0 | 0 | 0 | 0 |  |  |
| $C_{10}$ | 0 | 33 | 60 | 67 | 67 | 67 |  |  |
| $H_{10}$ | 0 | 13 | 33 | 60 | 60 | 60 |  |  |
| $J_{10}$ | 0 | 0 | 7 | 7 | 7 | 7 |  |  |
| $K_{10}$ | 0 | 0 | 47 | 67 | 73 | 73 |  |  |

The subscript denotes concentration in mg/liter.

Efficacy Against Adult C. fluminea

The nonionic alcohols demonstrated excellent efficacy against C. fluminea, as shown in Table 4. The performance against C. fluminea follows the order D>E>G>J>H>F>C.

The disubstituted amide of fatty acid, Chemical K, provided excellent efficacy against C. fluminea and would be ranked between Chemicals G and H for the nonionic alcohols.

The performance of the ether compound, Chemical L, was average and would fall between Chemicals F and C of the nonionic alcohols.

The overall ranking of chemicals from this invention against C. fluminea is in the order D>E>G>K>J>H>F>L>C.

TABLE 4

Efficacy Against C. fluminea

| Chemical | \multicolumn{8}{c}{Days of Observation} |
|---|---|---|---|---|---|---|---|---|
|  | 1 | 2 | 3 | 4 | 5 | 6 | 7 | 8 |
| \multicolumn{9}{l}{4A. Cumulative Mortality for Continuous Chemical Exposure} |
| Controls | 0 | 0 | 0 | 0 | 0 | 0 | 0 | 0 |
| $A_{10}$ | 0 | 0 | 0 | 0 | — | 0 |  |  |
| $B_{10}$ | 0 | 0 | 0 | 0 | 0 | 0 |  |  |
| $C_{10}$ | 0 | 0 | 0 | 0 | 13 | 87 |  |  |
| $D_{.25}$ | 0 | 0 | 0 | 0 | 0 | 0 | 0 | 0 |
| $D_1$ | 0 | 7 | 7 | 7 | 7 | 20 | 20 | 27 |
| $D_5$ | 0 | 0 | 0 | 0 | 0 | 40 | 40 | 40 |
| $D_{10}$ | 60 | 73 | 87 | 87 | 100 | 100 | 100 | 100 |
| $E_{10}$ | 20 | 53 | 80 | 100 | 100 | 100 |  |  |
| $F_5$ | 0 | 0 | 0 | 0 | 0 | 0 |  |  |
| $F_{10}$ | 0 | 0 | 20 | 47 | 100 |  |  |  |
| $G_5$ | 0 | 0 | 47 | 80 | 100 | 100 |  |  |
| $G_{10}$ | 0 | 13 | 47 | 100 | 100 |  |  |  |
| $H_5$ | 0 | 0 | 13 | 20 | 80 | 93 |  |  |
| $H_{10}$ | 0 | 0 | 33 | 73 | 100 |  |  |  |
| $I_{10}$ | 0 | 0 | 0 | 0 | 0 |  |  |  |
| $J_5$ | 0 | 0 | 0 | 0 | 0 | 0 |  |  |
| $J_{10}$ | 0 | 0 | 40 | 80 | 100 |  |  |  |
| $K_{.25}$ | 0 | 0 | 0 | 0 | 0 | 0 | 0 | 0 |
| $K_1$ | 0 | 7 | 7 | 7 | 7 | 7 | 7 | 7 |
| $K_5$ | 7 | 7 | 13 | 13 | 27 | 33 | 47 | 47 |
| $K_{10}$ | 0 | 7 | 47 | 87 | 100 | 100 | 100 | 100 |
| $L_{10}$ | 0 | 0 | 33 | 60 | 87 |  |  |  |
| $M_5$ | 0 | 0 | 0 | 0 | 0 |  |  |  |
| $M_{10}$ | 0 | 0 | 0 | 0 | 0 |  |  |  |
| $N_5$ | 0 | 0 | 0 | 0 | 0 |  |  |  |
| $N_{10}$ | 0 | 0 | 0 | 0 | 0 |  |  |  |
| \multicolumn{9}{l}{4B. Latent Mortality After 24 Hours Chemical Exposure} |
| $D_{10}$ | 0 | 0 | 0 | 0 | 0 | 0 |  |  |
| $C_{10}$ | 7 | 47 | 53 | 87 | 87 | 87 |  |  |
| $H_{10}$ | 0 | 29 | 29 | 71 | 71 | 71 |  |  |
| $J_{10}$ | 0 | 13 | 47 | 73 | 73 | 73 |  |  |
| $K_{10}$ | 0 | 7 | 7 | 7 | 7 | 7 |  |  |

The subscript denotes concentration in mg/liter.

Syphon and Feeding Activity

Observation of altered syphoning activity was recorded daily. These observations are useful to determine sublethal responses to various concentrations of chemicals. In general, D. polymorpha exhibited less avoidance of chemical exposure than did C. fluminea which is useful to understand differences in efficacy. When combined with other stress indicating observations it will be apparent to those skilled in the art that impairing the mollusc's ability to avoid chemical exposure renders it susceptible to synergistic treatments with toxicants such as chlorine.

Inhibition of Attachment

Unattached D. polymorpha were placed into chemically treated environments at various concentrations and their natural response to attach to available substratum was observed and recorded. The results are shown in Table 5. These observations are most useful in a preventive control treatment regime. Many of the chemicals exhibited excellent control.

The nonionic alcohols performance could be ranked in the order A=C=D=E=F=G=H>J>I>B.

The performance of the disubstituted amide of fatty acid, Chemical K, is equal to the best of the nonionic alcohols.

The performance of the ether compound, Chemical L, was excellent and comparable to the best of the nonionic alcohols.

The performance of the amphoteric compounds against attachment was low. When compared to the nonionic alcohols Chemical M and N would fall after Chemical B.

The overall ranking of chemicals from this invention against attachment of D. polymorpha is in the order A=C=D=E=F=G=H=K=L>J>I>B>M>N.

TABLE 5

Percent Inhibition of Attachment for *D. polymorpha*

| Chemical | Days of Observation | | | | | | | |
|---|---|---|---|---|---|---|---|---|
| | 1 | 2 | 3 | 4 | 5 | 6 | 7 | 8 |

4A. Cumulative Mortality for Continuous Chemical Exposure

| Chemical | 1 | 2 | 3 | 4 | 5 | 6 | 7 | 8 |
|---|---|---|---|---|---|---|---|---|
| Controls | <20 | <20 | <20 | <20 | <20 | <20 | <20 | <20 |
| $A_{10}$ | 100 | 100 | 100 | 100 | - | 100 | | |
| $B_{10}$ | 87 | 87 | 93 | 100 | 100 | | | |
| $C_{10}$ | 100 | 100 | — | 100 | 100 | 100 | | |
| $D_{.25}$ | 27 | 27 | 13 | 7 | 7 | 13 | 0 | 0 |
| $D_1$ | 80 | 40 | 47 | 47 | 40 | 50 | 25 | 8 |
| $D_5$ | 53 | 40 | 13 | 13 | 13 | 13 | 27 | 21 |
| $D_{10}$ | 100 | 100 | 100 | 100 | | | | |
| $E_{10}$ | 100 | 93 | 100 | 100 | | | | |
| $F_5$ | 100 | 73 | 7 | 13 | 13 | 7 | | |
| $F_{10}$ | 100 | 100 | 100 | 100 | 100 | | | |
| $G_5$ | 20 | 27 | 33 | 20 | 15 | 8 | | |
| $G_{10}$ | 100 | 100 | 100 | 100 | 100 | | | |
| $H_5$ | 100 | 0 | 100 | 100 | 100 | 100 | | |
| $H_{10}$ | 100 | 100 | 100 | 100 | 100 | | | |
| $I_{10}$ | 100 | 93 | 93 | 80 | 60 | | | |
| $J_5$ | 0 | 7 | 0 | 0 | 0 | 0 | | |
| $J_{10}$ | 93 | 100 | 100 | 100 | 100 | | | |
| $K_{.25}$ | 53 | 33 | 7 | 7 | 7 | 7 | 7 | 7 |
| $K_1$ | 87 | 67 | 60 | 60 | 27 | 20 | 20 | 20 |
| $K_5$ | 100 | 73 | 100 | | | | | |
| $K_{10}$ | 100 | 100 | 100 | | | | | |
| $L_{10}$ | 100 | 100 | 100 | 100 | 100 | | | |
| $M_5$ | 60 | 53 | 40 | 27 | 7 | | | |
| $M_{10}$ | 67 | 87 | 93 | 87 | 93 | | | |
| $N_5$ | 47 | 40 | 53 | 33 | 7 | | | |
| $N_{10}$ | 73 | 73 | 87 | 80 | 100 | | | |

5B. Latent Effects On Inhibition After 24 Hours Chemical Exposure

| | 1 | 2 | 3 | 4 |
|---|---|---|---|---|
| $D_{10}$ | 100 | 100 | 67 | 38 |
| $C_{10}$ | 87 | 80 | 50 | 16 |
| $H_{10}$ | 80 | 53 | 39 | 40 |
| $J_{10}$ | 87 | 33 | 13 | 0 |
| $K_{10}$ | 100 | 100 | 67 | 38 |

The subscript denotes concentration in mg/liter.

Chemical Effect on Byssal Threads

While not intending to be bound by any theory, it is believed that the tests show that the amphoteric group, and in particular amino acid derivatives, produce a direct effect on the preformed byssal threads. This effect in manifest as short term embrittlement of the normally elastic byssal thread. The attached molluscs are then susceptible to release by the normal hydraulic regime within water systems. This discovery is most useful to the mitigation of attached mollusc and specifically for *D. polymorpha*. This method has exceptional merit over conventional methods of mechanical or aggressive chemical (i.e., mineral acids) approaches to system cleaning. This mitigating effect is distinguished from that of inhibiting byssal attachment of unattached mollusc.

Exportation of the Diurnal Response

The normal diurnal response of greater syphon activity and feeding by molluscs during the hours of darkness is well documented in the literature. This instinctive response was observed in the laboratory under artificial lighting systems. Therefore, the use of controlled lighting inside water intakes and related structures is a means to minimize chemical requirements for effective control of molluscs. The diurnal response may be utilized to optimize chemical injection and to exploit this natural mollusc activity peak.

Summary of Chemical Performance

This invention provides a wide range of chemicals which work effectively to perform one or more effects which are important to mollusc control. The side-by-side comparison of the tested chemicals and their effect(s) is presented in Table 6. From this presentation, those skilled in the art will be able to select the desired effects from one or a combination of the chemicals tested and to be more effective against each species of mollusc.

TABLE 6

Performance Comparison of All Chemicals

| Chemical | Type | M1 | M2 | M3 | A |
|---|---|---|---|---|---|
| A | Nonionic Alcohol | 8 | 10 | — | 1 |
| B | Nonionic Alcohol | 14 | 12 | — | 4 |
| C | Nonionic Alcohol | 11 | 6 | 9 | 1 |
| D | Nonionic Alcohol | 5 | 2 | 1 | 1 |
| E | Nonionic Alcohol | 2 | 3 | 2 | 1 |
| F | Nonionic Alcohol | 12 | 7 | 7 | 1 |
| G | Nonionic Alcohol | 4 | 5 | 3 | 1 |
| H | Nonionic Alcohol | 3 | 4 | 6 | 1 |
| I | Nonionic Alcohol | 6 | 14 | — | 3 |
| J | Nonionic Alcohol | 9 | 9 | 5 | 2 |
| K | Amide | 1 | 1 | 4 | 1 |
| L | Ether | 7 | 8 | 8 | 1 |
| M | Amphoteric | 13 | 13 | — | 5 |
| N | Amphoteric | 10 | 11 | — | 6 |

NOTES FOR TABLE 6:
M1 = Mortality against attached *D. polymorpha*
M2 = Mortality against unattached *D. polymorpha*
M3 = Mortality against *C. fluminea*
A = Control of attachment It will be apparent to those skilled in the art that there are various applications for the method of the present invention which include, but are not limited to, control and mitigation of macrofouling of molluscs in various aqueous systems such as fresh and saline water supplies used for industrial, steam, electric, municipal and similar applications where macrofouling may cause impairment of system performance. Specific water systems which may be protected according to the method of the present invention include, but are not limited to, once-through and recirculating cooling waters, potable water systems, fire protection systems and other types of auxiliary water systems.

What is claimed:

1. A method for controlling the proliferation of mollusks comprising *Dreissena polymorpha* or *Corbicula fluminea* in a target habitat comprising the step of applying to said habitat a proliferation controlling effective amount of a compound or mixture of compounds selected from the group consisting of N,N-disubstituted fatty acid amides, fatty acid alkanolamides and ethoxylated or propoxylated derivatives of said amides and said alkanolamides; nonionic polyethoxylated or polypropoxylated primary and secondary alkyl and aryl alcohols; nonionic block copolymers of ethylene oxide and propylene oxide; amphoteric fatty acid substituted-alkyl aminocarboxylic acids, fatty acid substituted amidosulfates and fatty acid substituted aminosulfates and fatty acid substituted aminosulfonates.

2. A method according to claim 1 wherein said effective amount is sufficient to inhibit proliferation of unattached molluscs in said habitat.

3. A method according to claim 1 wherein said effective amount is sufficient to inhibit proliferation of attached molluscs in said habitat.

4. A method according to claim 3 wherein said effective amount effectively embrittles the byssal threads of said molluscs.

5. A method according to claim 1 wherein said effective amount is from about 1–20 mg/liter in said habitat.

6. A method according to claim 4 wherein said compounds comprise said aminocarboxylic acids, amidosulfates, aminosulfates or aminosulfonates.

7. A method according to claim 1 wherein said amides, alkanolamides, nonionic alcohols and block copolymers are characterized by a cloud point up to 75° C. and HLB values in the range of about 5 to 15.

8. A method according to claim 7 wherein said N,N-disubstituted amide fatty acids comprise N,N-disubstituted amides of tall oil fatty acids.

9. A method according to claim 7 wherein said alcohol comprises nonionic octylphenoxy polyethoxy ethanol.

10. A method according to claim 7 wherein said alcohols comprise nonionic nonylylphenoxy polyethoxy ethanol.

11. A method according to claim 7 wherein said block copolymers comprise polyalkylene glycol ethers.

* * * * *

UNITED STATES PATENT AND TRADEMARK OFFICE
CERTIFICATE OF CORRECTION

PATENT NO. : 5,503,836

DATED : April 2, 1996

INVENTOR(S) : Fellers et al.

It is certified that error appears in the above-indentified patent and that said Letters Patent is hereby corrected as shown below:

In column 6, line 21, change "$C_{10}$" to read --$G_{10}$--.
In column 7, line 24, change "$C_{10}$" to read --$G_{10}$--.
In column 8, line 20, change "$C_{10}$" to read --$G_{10}$--.
In column 9, line 3, change "Percent" to read --5A.Percent--.
In column 9, line 8, delete --4A. Cumulative Mortality for Continuous Chemical Exposure--.

In column 9, line 35, change "$C_{10}$" to read --$G_{10}$--.

Signed and Sealed this

Twenty-fifth Day of November, 1997

*Attest:*

*Attesting Officer*

BRUCE LEHMAN

*Commissioner of Patents and Trademarks*